United States Patent [19]

Takao et al.

[11] 4,126,532
[45] Nov. 21, 1978

[54] OXYGEN SENSOR

[75] Inventors: Hiroshi Takao, Kamakura; Kazuo Matoba, Yokosuka, both of Japan

[73] Assignee: Nissan Motor Company, Limited, Yokohama, Japan

[21] Appl. No.: 835,230

[22] Filed: Sep. 21, 1977

[30] Foreign Application Priority Data

Sep. 22, 1976 [JP] Japan .................................. 51-114304

[51] Int. Cl.² ............................................. G01N 27/58
[52] U.S. Cl. .................................................. 204/195 S
[58] Field of Search ................ 204/15, 195 S; 60/276; 123/119 E; 324/29; 23/254 E

[56] References Cited

U.S. PATENT DOCUMENTS

| 3,578,578 | 5/1971 | von Krusenstierna | 204/195 S |
| 4,040,929 | 8/1977 | Bauer et al. | 204/195 S |

FOREIGN PATENT DOCUMENTS 2,304,464  8/1974  Fed. Rep. of Germany ....... 204/195 S Primary Examiner—G. L. Kaplan
Attorney, Agent, or Firm—Bacon & Thomas

[57] ABSTRACT

A first layer of a metal/metal oxide sinter which acts as a reference source of oxygen is affixed on a flat surface of a base member, a second layer of solid electrolyte is affixed on the first layer and a third layer of metal is affixed on the second layer so that upon exposure of the third layer to exhaust gases or the like, an EMF (electromotive force) is developed between the first and third layers.

6 Claims, 6 Drawing Figures

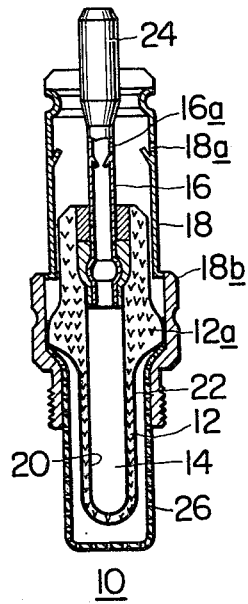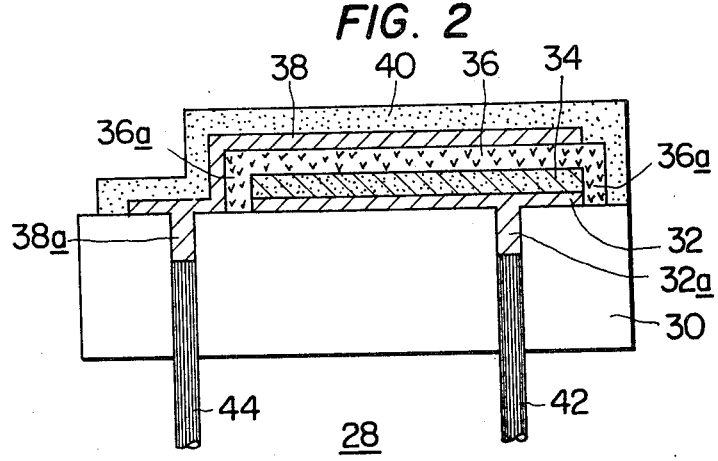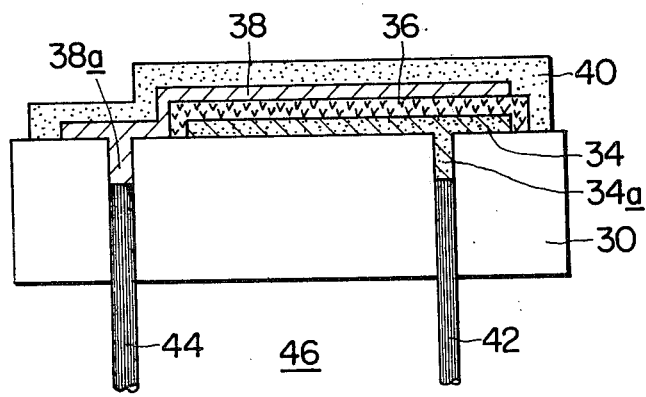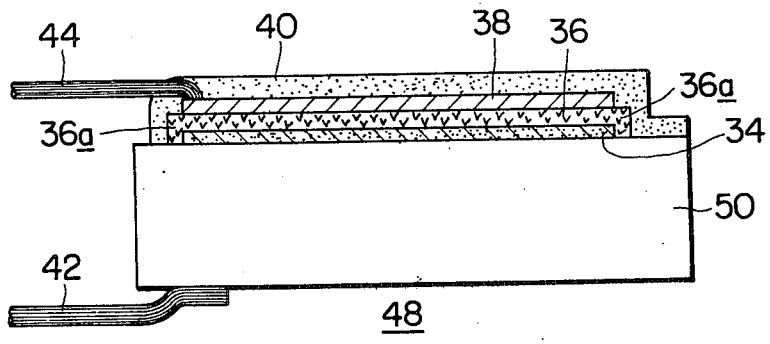

OXYGEN SENSOR

BACKGROUND OF THE INVENTION

The present invention relates in general to an electrochemical sensing device to determine oxygen content in a gas or a liquid utilizing an ion conductive solid electrolyte to form an oxygen concentration cell, and more particularly to an oxygen sensor of the type mentioned above for use with a closed loop air-fuel mixture supply control system of an automotive internal combustion engine.

SUMMARY OF THE INVENTION

It is an object of the present invention to provide a new and improved oxygen sensor which can exhibit its maximum possible electromotive force (EMF) even when used in a relatively low temperature gas in which conventional oxygen sensors exhibit quite poor performance.

It is another object of the present invention to provide a new and improved oxygen sensor which is simple in construction and is compact, inducing a relatively low production cost thereof.

According to the present invention, there is provided an oxygen sensor for determining the oxygen content in a non-conductive base member having thereon a substantially flat surface and therein spaced first and second through holes which extend from the flat surface; a first layer having a function to act as a reference source of oxygen and having first and second surfaces, the first surface of the first layer being directly affixed to the flat surface of the base member to cover the first through hole; a portion of the first layer, the portion being received in the first through hole; a second layer of a solid electrolyte covering the first layer and having first and second surfaces, the first surface of the second layer being directly affixed to the second surface of the first layer; a third layer of a metal covering the second layer and having first and second surfaces, the first surface of the third layer being directly affixed to the second layer, the second surface of the third layer being exposed to the fluid; a portion of the third layer, the portion being received in the second through hole in the base member; and two lead wires respectively received in the first and second through holes to be connected with the portions of the first and third layers, respectively.

Other objects and advantages of the present invention will become clear from the following description when taken in conjunction with the accompanying drawings.

BRIEF DESCRIPTION OF THE DRAWING

FIG. 1 is a sectional view of a conventional oxygen sensor;

FIG. 2 is a sectional view of an oxygen sensor embodying the present invention;

FIG. 3 is a similar view to FIG. 2, but showing another embodiment of the invention;

FIG. 4 is also a similar view to FIG. 2, but showing still another embodiment of the invention;

DETAILED DESCRIPTION OF PREFERRED EMBODIMENTS

Figure 5:
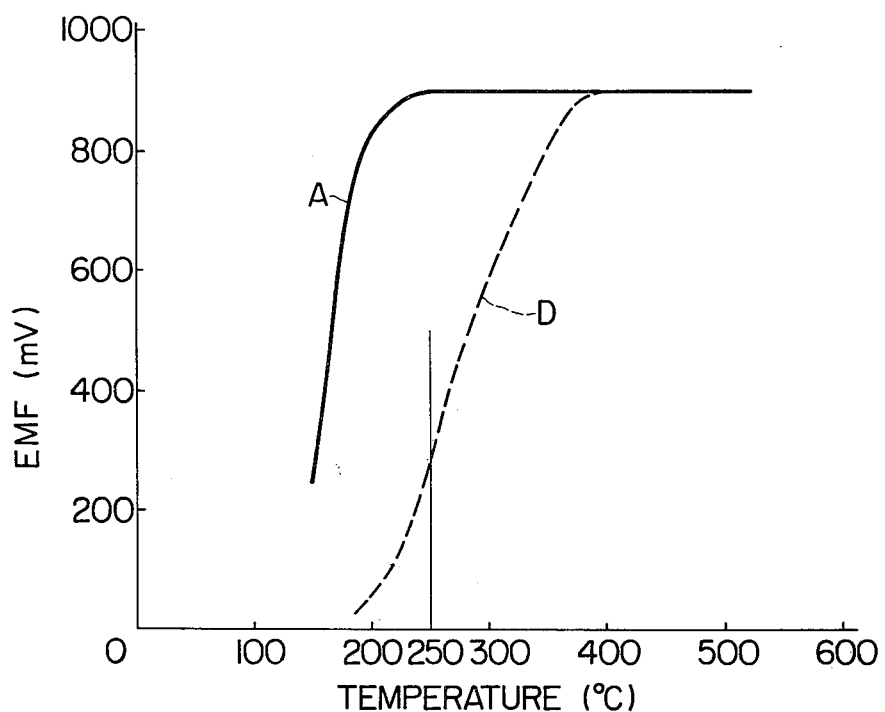
FIG. 5 is a graph showing qualitatively the relationship between the temperature of a gas under measurement and the magnitude of EMF developed in the oxygen sensors of FIGS. 1 to 4.

In order to clarify the inventive steps of the present invention, a description of a prior art oxygen sensor will be given with the aid of FIG. 1.

In this figure, the conventional oxygen sensor is shown as generally designated by numeral 10. The sensor comprises a tubular solid electrolyte 12 having one end closed and the other end open. The electrolyte 12 is formed at its axially middle portion with a collar portion 12a for the reason which will be apparent hereinafter. Denoted by numeral 14 is a hollow space defined within the electrolyte 12 which is in communication with the open air via openings 16a and 18a formed respectively in a metallic tube 16 and a metallic tubular casing 18. The air thus fed into the space 14 functions as a reference gas or reference source of oxygen. The surface defining the hollow space 14 of the electrolyte is coated or covered with a thin metallic electrode 20, such as a platinum layer, the electrode being in electrical contact with the metallic tube 16. The tubular casing 18 has an enlarged section 18b within which the collar portion 12a of the electrolyte is snugly received so that another thin electrode 22, also made of a platinum and which covers the outer surface of the electrolyte 12, electrically contacts the casing, as shown. Numeral 24 is a terminal member connected to the thin electrode 20 through the metallic tube 16. The closed end portion of the electrolyte 12 projects into a perforated sleeve 26 which is fixed at its upper end to the tubular casing 18. With this construction, an electromotive force (EMF) is developed between the casing 18 and the terminal member 24 upon exposing the sensor 10 to a gas the oxygen concentration of which is to be measured, or as it will be referred to hereinafter, the gas under measurement.

In this conventional oxygen sensor 10, however, there arises the following drawbacks: First, because of the complicated configuration of the tubular electrolyte 12 having the collar portion 12a and the hollow space 14, the formation of such electrolyte 12 requires or involves troublesome production steps. Second, since the electrolyte 12 is complex in structure as mentioned above, the assemblage of the electrolyte 12 with the other parts such as the casing 18 and the metallic tube 16 becomes very difficult. Third, since the electrolyte 12 is formed into a tube, it is liable to be cracked or broken by slight shocks. U.S. Pat. No. 3,940,327 discloses an oxygen sensor which partially solves the above drawbacks. This sensor comprises a disc-shaped solid electrolyte having opposite flat surfaces which are respectively coated or covered with two thin metallic electrodes, and which is disposed in one end of a metallic tube. However several drawbacks are still encountered even in this sensor because of its structural complication.

From the above, it will be apparent that there is a limitation, in the prior art oxygen sensor, with respect to the ability of making the entire sensor construction compact and simple. In fact, a rather bulky solid electrolyte having a detecting section of about 0.5 to 1.0 mm in thickness has been widely used for the oxygen sensor. This is because, if the thickness of the section is less than 0.5 mm, it lacks adequate mechanical strength. In addition, in the conventional oxygen sensor shown in FIG. 1, sometimes the connection between the outer electrode 22 covering the outer surface of the electrolyte 12 and the inner surface of the metallic casing 18 becomes loose due to vibrations applied thereto during its use, thereby disturbing the electrical connection therebetween. With this, the gas under measurement may penetrate into the open air space via a clearance thus formed in the sensor, thereby preventing the sensor from exhibiting its normal performance.

In the oxygen sensors of the type mentioned above, there is a tendency that the electromotive force (EMF) of the electrolyte is critically dependent on the temperature of the same. More specifically, the magnitude of EMF is reduced as the temperature of the electrolyte lowers. In fact, common oxygen sensors cannot exhibit their maximum possible performances when used in a gas having a temperature lower than about 250° C. This means that the above mentioned sensors fail to accurately determine the oxygen content of the exhaust gases emitted from an idling internal combustion engine since the temperature of the exhaust gases under such condition is inevitably lower than 250° C. In view of the above, common oxygen sensors are often arranged in a gas stream under measurement so as to locate the detecting section thereof in the highest possible temperature zone of the stream. This arrangement, however, causes overly elongated construction of the sensor.

In order to solve the above-stated several drawbacks, an oxygen sensor has been developed which comprises a base member of a sintered mass made of a mixture of metal and an oxide of the metal, such as a mixture of Ni-NiO, a solid electrolyte layer deposited on a surface of the sintered base member, and an electrically conductive layer, such as a platinum layer, disposed on the solid electrolyte layer. This type of oxygen sensor has solved the afore-mentioned drawbacks to some extent; however there arises a problem in the sensor, i.e., the atmospheric air reaches the contacting surfaces of the mass and the solid electrolyte layer through the porous sintered mass (base member) thereby preventing the sensor from functioning optimally. This undesirable phenomenon becomes more notable as the thickness of the sintered mass is reduced below about 1 mm.

Referring to FIG. 2 of the drawings, there is illustrated an oxygen sensor, according to a first embodiment of the invention, as generally designated by numeral 28. The sensor 28 comprises a solid base member 30 made of ceramics or a mixture of ceramics and metal. On an upper flat surface of the base member 30 is deposited an electrically conductive layer 32, such as a platinum layer, which acts as an electrode. Disposed on an upper surface of the layer 32 is a layer 34 of an oxygen containing material such as a mixture of a metal and an oxide of the metal. A solid electrolyte layer 36 is deposited on an upper surface of the oxygen containing layer 34 while covering lateral edges of the layers 32 and 34 by its downwardly bent portions or flanges 36a. The leading ends of the bent portions 36a sealingly contact the upper flat surface of the base member 30, as shown. The outer or upper surface of the electrolyte layer 36 is covered with another electrically conductive layer, such as a platinum layer, 38 acting as another electrode of the electrolyte 36. A porous protecting layer 40 covers the conductive layer 38 and a part of the electrolyte layer 36 as a protection against mechanical and chemical damage. As shown, the electrode layers 32 and 38 are formed with respective projections 32a and 38a which are received in holes (no numerals) formed in the base member 30. First and second terminal members 42 and 44 are respectively held in the holes to be connected to the respective projections 32a and 38a. With this construction, the electromotive force (EMF) is developed across the first and second terminal members 42 and 44 upon exposing the sensor 28 to a gas under measurement.

In FIG. 3, an oxygen sensor according to a second embodiment of the invention is shown as being generally designated by numeral 46. This oxygen sensor 46 comprises generally the same parts as in the case of the above-stated first embodiment 28. Thus, the same parts are designated by the same numerals as in FIG. 2. In this second embodiment, the first mentioned electrode 32 in the sensor 28 (see FIG. 2) is omitted and therefore the oxygen containing layer 34 is formed with a projection 34a connected to the first terminal member 42.

In FIG. 4, an oxygen sensor according to a third embodiment of the invention is shown as generally designated by numeral 48. Also in this Figure, generally the same parts are denoted by the same numerals as in the case of FIG. 2. The oxygen sensor 48 comprises a base member 50 which may be constructed of a rolled steel or a conventional sintered metal. On an upper flat surface of the base member 50 is deposited a layer of an oxygen-containing material 34, such as a mixture of a metal and an oxide of the metal. This layer 34 functions as an electrode as well as a reference source of oxygen. A layer 36 of a solid electrolyte is deposited on an upper surface of the oxygen-containing material layer 34 while covering lateral edges of the same by its downwardly bent ends 36a. The leading ends of the bent ends 36a are in sealing contact with the upper flat surface of the base member 50. An upper surface of the solid electrolyte layer 36 is covered with a layer 38 of an electrically conductive material acting as another electrode of the electrolyte 36. A porous protecting layer 40 covers the electrode 38 and the downwardly bent ends 36a of the electrolyte 36, as shown, as a protection against mechanical and chemical damage. A first terminal member 42 is connected to a lower surface of the base member 50 by means of welding or the like, and a second terminal member 44 is connected to electrode 38 passing through an opening (no numeral) formed in the protecting layer 30. The electromotive force (EMF) is developed across the two terminal members 42 and 44 upon exposure of the sensor 48 to a gas under measurement.

In the sensors of the invention stated above, the oxygen-containing material 34 may consists of a mixture of Ni-NiO, Cd-CdO, Zn-ZnO, Cu-$Cu_2O$, Co-CoO or Cr-$Cr_2O_3$. Each mixture may be made of 1 to 99% metal composition and the balance of metal oxide. Experiments have revealed that the mixture of Ni-NiO provides most satisfactory results in the invention. The solid electrolyte 36 may consists of $ZrO_2$ stabilized by CaO, $Y_2O_3$, SrO, MgO or $ThO_2$, or $Bi_2O_3$ stabilized by $Nb_2O_5$, SrO, $WO_3$, $Ta_2O_5$ or $Y_2O_3$. In addition, conventional mixtures such as $ThO_2$-$Y_2O_3$ and CaO-$Y_2O_3$ may also be used to form the electrolyte 36 in this invention. For formation of the electrode layers 32 and 38, materials devoid of catalytic oxidizing properties (such as Ag, Au and SiC) as well as materials having catalytic oxidizing properties (such as Ru, Rh, Pd, Os, Ir and Pt) are both usable. Furthermore, alloys of the platinum group metals (such as Ru, Rh, Pd, Os, Ir and Pt) and alloys of these platinum group metals and base metals may be used for the electrode layers 32 and 38 in this invention. The porous protecting layer 40 may be made of $Al_2O_3$, BeO, $ZrO_2$, SiC and/or any other known ceramic materials.

EXAMPLE 1

To prepare an oxygen sensor such as one shown in FIG. 2, the following procedure was followed. For the base member 30, an alumina plate having a purity of above 98% and 5 mm in length, 5 mm in width and 0.5 mm in thickness was used. For accommodation of the two terminal members 42 and 44, two through holes having the same diameter of about 0.5 mm were formed in the base member 40. The first electrode layer 32 was prepared on the base member 30 by coating the upper flat surface of the base member 30 with a paste containing platinum powder dispersed in an organic binder and then baking the coated base member 30 at about 1400° C. The paste was not applied to a limited zone where the through hole for the terminal member 44 was positioned. With this procedure, a platinum layer having a thickness of about 2 microns was provided on the base member 30. For formation of the oxygen-containing layer 34, a mixture of 50 Wt% Ni and 50 Wt% NiO (having a particle size from about 0.2 microns to about 10 microns) was applied to the upper surface of the electrode layer 32 to cover the same and then baked at about 1300° C. for about 1 hr in air. With this, a fixed layer of Ni and NiO having a thickness of about 30 microns was made. The solid electrolyte layer 36 was prepared by applying a mixture of 15 mole% $Nb_2O_5$ and 85 mole% $Bi_2O_3$ (having a particle size ranging from about 0.1 microns to 5 microns) to the Ni-NiO layer 34 and the lateral ends of the electrode layer 32 and the layer 34, and after drying the mixture, baking it at about 920° C. With this, an electrolyte layer having a thickness of about 20 microns was produced. The same paste as used to produce the first layer was applied to the surface of the electrolyte layer 36 and to the before-mentioned limited zone and baked at about 900° C. for about 1 hr. By this procedure, a platinum layer having a thickness of about 2 microns was produced. By using a plasma-jet-depositing method, a porous alumina layer was formed on the electrode 38, the partially naked portion 36a of the electrolyte 36 and or a portion of the base member 30. The thickness of the porous alumina layer 40 was about 50 microns. Stainless steel twisted wires (SUS 304) having a diameter of about 0.5 mm were disposed in the respective through holes of the base member 30 and connected to the respective electrode layers 32 and 38 via brazing techniques (silver solder: BAg-1, soldering temperature: 650° C.).

The oxygen sensor 28 provided via the above-mentioned procedure was subjected to an experiment to examine the EMF characteristic in a combusted gas stream of propane with respect to the temperature of the gas. The result of the experiment is shown by the line A of the graph of FIG. 5. For comparison, a result of a conventional oxygen sensor, such as one shown in FIG. 1, equipped with a tubular solid electrolyte (15 mole% CaO + 85 mole% $ZrO_2$) having a thickness of about 1.0 mm is also shown by a dotted line D. As well seen from this graph, the sensor 28 according to the invention exhibits the maximum possible EMF even when the temperature of the combusted gas stream is about 250° C. as compared with the conventional sensor which exhibits a greatly reduced EMF at the same temperature.

Figure 6:
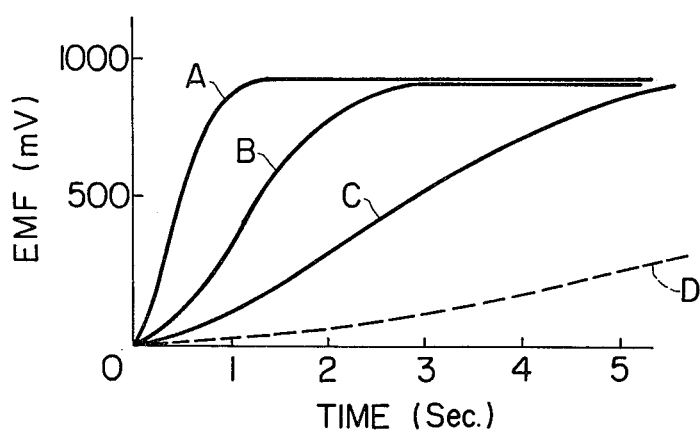
FIG. 6 is a graph showing qualitatively the relationship between the time for which the sensor is exposed to a gas the oxygen concentration of which is to be measured and the EMF developed by the same for various oxygen sensors including those of the invention.

The oxygen sensor 28 was subjected to another experiment to examine the relationship between the EMF developed by the sensor and the exposure time to the combusted gas stream having a constant temperature of about 250° C. The result of this experiment is shown in FIG. 6 by a solid line A. Solid lines B and C show respective results of two conventional oxygen sensors, the first of which comprises a disc-shaped sintered mass made of a mixture of Ni-NiO, the thickness of the mass being about 1 mm, a solid electrolyte layer made of a solid solution of 15 mole% $Nb_2O_5$ and 85 mole% $Bi_2O_3$ having a thickness of about 50 microns, the electrolyte layer being deposited on one surface of the sintered mass, and an platinum layer about 2 microns thick deposited on the electrolyte, and the second of which comprises a cylindrical sintered mass of about 5 mm long made of the Ni-NiO mixture, an about 0.5 mm thick solid electrolyte made of 15 mole% $Nb_2O_5$ and 85% $Bi_2O_3$ and deposited on one surface of the sintered mass, and a 2 micron thick layer of platinum deposited on the electrode. A broken line D shows the result of the before-mentioned conventional oxygen sensor shown in FIG. 1. As shown in this graph, the sensor 28 of the subject invention exhibits rapid warm-up characteristics and produces the maximum possible EMF in the minimum possible time.

EXAMPLE 2

To prepare an oxygen sensor such as one shown in FIG. 3, the following steps were taken. Substantially the same procedure was followed as in Example 1, but the step of forming the first electrode layer 32 was omitted in this Example 2 so that the sintered layer 34 also functioned as an electrode. Substantially the same performance was obtained as in Example 1.

EXAMPLE 3

To prepare an oxygen sensor such as one shown in FIG. 4, the following steps were taken. For the base member 50, a stainless steel plate (SUS 430) 5 mm in length, 5 mm in width and 0.3 mm in thickness was used. For the first terminal member 42, a stainless steel wire (SUS 304) having a diameter of about 0.5 mm soldered to the back surface of the base member 50 was employed. The upper surface of the stainless steel plate (the base member 50) was polished by using $\pi$500 grade emery paper and the polished surface was rinsed with alcohol and then dried. For formation of the oxygen-containing layer 34, the same Ni-NiO mixture as in Example 1 was applied on the clean dried surface of the base member 50 and then baked at about 1150° C. The solid electrolyte layer 36 and the platinum layer 38 were prepared via the same procedure as in Example 1. A stainless steel wire (SUS 304) having a diameter of about 0.1 mm was soldered to a portion of the platinum layer 38. By using the plasma-jet-depositing method, a porous alumina layer 40 was formed on the platinum layer 38. With this construction, the oxygen sensor 48 exhibited substantially the same performance as in the case of Example 1.

What is claimed is:

1. An oxygen sensor for determining the oxygen content in a fluid, comprising:
    a non-conductive base member having thereon a substantially flat surface and having spaced first and second holes passing therethrough which extend from said flat surface;
    a first layer of solid material providing a reference source of oxygen and having first and second surfaces, said first surface of said first layer being directly affixed to said flat surface of said base member and covering said first hole, with a portion of said first layer being received in said first hole;

a second layer of a solid electrolyte covering said first layer and having first and second surfaces, said first surface of said second layer being directly affixed to said second surface of said first layer;

a third layer of a metal covering said second layer and having first and second surfaces, said first surface of said third layer being directly affixed to said second surface of said layer, said second surface of said third layer being exposed to said fluid, and a portion of said third layer being received in said second hole in said base member; and two lead wires respectively received in said first and second holes and connected with the portions of said first and third layers, respectively received in said holes.

2. An oxygen sensor as claimed in claim 1, wherein said first layer comprises a compacted powder mixture including a metal and an oxide of said metal.

3. An oxygen sensor as claimed in claim 2, wherein said first layer comprises a mixture of Ni and NiO.

4. An oxygen sensor as claimed in claim 1, wherein said first layer comprises:
- a first sub-layer of a compacted powder mixture comprising a metal and an oxide of said metal; and
- a second sub-layer of a metal interposed between said first sub-layer of said compacted powder mixture and said flat surface of said base member, said second sublayer of said metal constituting said portion of said first layer received in said first hole.

5. An oxygen sensor as claimed in claim 1, further comprising a porous protecting layer which covers the second surface of said third layer, said porous protecting layer being comprised of a ceramic.

6. An oxygen sensor as claimed in claim 1, wherein said base member is made from a material selected from the group consisting of a ceramic and a mixture of a ceramic and a metal.

* * * * *